United States Patent
Gabriel et al.

(10) Patent No.: US 6,677,459 B2
(45) Date of Patent: Jan. 13, 2004

(54) AMINO ACID DERIVATIVES AND METHODS OF MAKING THE SAME

(75) Inventors: Richard L. Gabriel, Swampscott, MA (US); Jurjus Jurayj, Acton, MA (US)

(73) Assignee: Johnson Matthey Pharmaceutical Materials, Inc., Devens, MA (US)

( * ) Notice: Subject to any disclaimer, the term of this patent is extended or adjusted under 35 U.S.C. 154(b) by 0 days.

(21) Appl. No.: 10/427,466

(22) Filed: Apr. 30, 2003

(65) Prior Publication Data

US 2003/0208083 A1 Nov. 6, 2003

Related U.S. Application Data

(60) Division of application No. 10/178,180, filed on Jun. 21, 2002, now Pat. No. 6,590,106, which is a division of application No. 09/342,855, filed on Jun. 29, 1999, now Pat. No. 6,479,669, which is a continuation-in-part of application No. 09/074,765, filed on May 8, 1998, now abandoned.
(60) Provisional application No. 60/046,129, filed on May 9, 1997.

(51) Int. Cl.$^7$ ............................................ C07D 233/61
(52) U.S. Cl. .................................................... 548/335.5
(58) Field of Search ...................................... 548/335.5

(56) References Cited

U.S. PATENT DOCUMENTS

| | | | |
|---|---|---|---|
| 4,864,051 A | | 9/1989 | Ramalingham |
| 5,200,561 A | | 4/1993 | Konya et al. |
| 5,475,138 A | | 12/1995 | Pal et al. |
| 5,684,157 A | * | 11/1997 | Griffiths et al. ........... 548/335.5 |
| 6,316,415 B1 | | 11/2001 | Albrecht et al. |
| 6,358,955 B1 | * | 3/2002 | Thurkauf et al. ....... 514/252.13 |
| 6,403,806 B1 | * | 6/2002 | Yeh et al. ................. 548/335.5 |
| 6,407,258 B1 | * | 6/2002 | Napierski et al. ........ 548/335.5 |
| 6,515,133 B1 | * | 2/2003 | Thurkauf et al. ......... 546/274.1 |

FOREIGN PATENT DOCUMENTS

| | | |
|---|---|---|
| WO | WO 94/04491 | 3/1994 |
| WO | WO 96/39399 | 12/1996 |
| WO | WO 97/09051 | 3/1997 |

OTHER PUBLICATIONS

Itsuno, S., et al., "Asymmetric Synthesis Using Chirally Modified Borohydrides. Part 3. Enantioselective reduction of Ketones and Oxime Ethers with Reagents Prepared from Borane and Chiral Amino Alcohols," *J. Chem. Soc. Perkin Trans.*, pp.: 2039–2044 (1985).
Sakito, Y., et al., "Asymmetric Reduction of Oxime Ethers. Distinction of Anti and Syn Isomers Leading to Enantiomeric Amines," *Tetrahedron Letters*, 29(2):223–224 (1988).
Brown, H.C., and Krishnamurthy, S., "Boranes for Organic Reductions—A Forty-Year Odyssey," *Aldrichimica Acta*, 12(1):3–11 (1979).

von Geldern, T.W., et al., "Azole Endothelin Antagonists. 1. A Receptor Model Explains an Unusual Structure—Activity Profile," *J. Med. Chem.*, 39:957–967 (1996).
Armstrong, R.W., et al., "Multiple–Component Condensation Strategies for Combinatorial Library Synthesis," *Acc. Chem. Res.*, 29:123–131 (1996).

(List continued on next page.)

*Primary Examiner*—Deborah C. Lambkin
(74) *Attorney, Agent, or Firm*—Hamilton, Brook, Smith & Reynolds, P.C.

(57) ABSTRACT

Disclosed are novel compounds represented by Structural Formula II, IX or XXVIII:

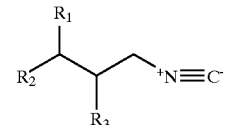

II.

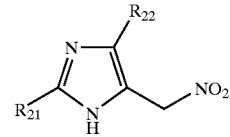

IX.

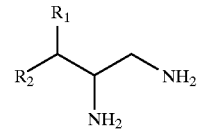

XXVII.

$R_1$, $R_{21}$, and $R_{22}$ are independently an aliphatic group, a substituted aliphatic group, an aromatic group or a substituted aromatic group.

$R_2$ is $-NR_4R_5$ or $-N^+\equiv C^-$.

Alternatively, $R_1$ and $R_2$, taken together with the methine group to which they are bonded, are a moiety represented by the following structural formula:

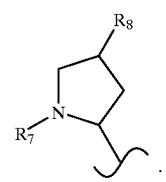

$R_3$ is $-NH_2$, $-OH$, $-OC(O)H$ or $-OR_9$.
$R_5$, $R_6$ and $R_7$ are independently $-H$ or an amine protecting group.
$R_8$ is $-H$, $-OH$ or $-OR_8$.
$R_9$ is an alcohol protecting group.

Also disclosed are methods of preparing these compounds.

3 Claims, No Drawings

OTHER PUBLICATIONS

Tempest, P.A., et al., "Solid–Phase, Parallel Syntheses by Ugi Multicomponent Condensation," *Angew. Chem. Int. Ed. Engl.*, 35(6):640–642 (1996).

Sandler, S.R., and Karo, W., "Organic Functional Group Preparations," vol. III, 2nd edition, Academic Press, Inc., San Diego, Chapter 8, pp. 206–234 (1989).

Ugi, I., et al., "Isonitrile Syntheses," *Angew. Chem. Int. Edit Engl.*, 4(6):472–484 (1965).

Walborsky, H.M., and Niznik, G.E., "Synthesis of Isonitriles," *J. Org. Chem.*, 37(2):187–190 (1972).

Skorna, G., and Ugi, I., "Isocyanide Synthesis with Diphosgene," *Angew. Chem. Int. Ed. Engl.*, 16(4):259–260 (1977).

Bestmann, H.J., et al., "Reaktionen zwischen Triphenylphosphin–dibromid und substituierten Säureamiden," *Liebigs Ann. Chem.*, 718:24–32 (1968). (With English abstract).

Sheehan, J.C. and Yang, D–D H., The Uses of N–Formylamino Acids in Peptide Synthesis, *J. Am. Chem. Soc.*, 80:1154–1158 (1958).

Jahngen, E.G.E.,Jr., and Rossomando, E.F., "The Synthesis of Hadacidin: Sodium Cyanoborohydride Reduction of $\alpha$–Oximinoic Acids," *Synth. Commun.*, 12(8):601–606 (1982).

Waki, M. and Meienhofer, J., "Efficient Preparation of $N^{\alpha}$–Formylamino Acid tert–Butyl Esters," *J. Org. Chem.*, 42(11):2019–2021 (1977).

Djuric, S.W., "A Mild and Convenient Procedure for the N–Formylation of Secondary Amines Using Organosilicon Chemistry," *J. Org. Chem,.* 49:1311–1312 (1984).

Houghten, R.A., et al., "The Use of Synthetic Peptide Combinatorial Libraries for the Determination of Peptide Ligands in Radio–Receptor Assays: Opioid Peptides," *Bioorganic & Medicinal Chemistry Letters*, 3(3):405–412 (1993).

ChemDiv. International Chemical Diversity. Synthetic Products. [online] (retrieved on Dec. 20, 2001] <URL://http://www.chemdiv.com/intchemdiv>.

* cited by examiner

AMINO ACID DERIVATIVES AND METHODS OF MAKING THE SAME

RELATED APPLICATIONS

This application is a divisional of U.S. application Ser. No. 10/178,180, filed Jun. 21, 2002, U.S. Pat. No. 6,590,106 which is a divisional of U.S. application Ser. No. 09/342,855, filed Jun. 29, 1999, now U.S. Pat. No. 6,479,669, which is a continuation-in-part of U.S. application Ser. No. 09/074,765, filed May 8, 1998, now abandon, which claims the benefit of U.S. Provisional Application No. 60/046,129, filed May 9, 1997. The entire teachings of the above applications are incorporated herein by reference.

BACKGROUND OF THE INVENTION

A peptide mimetic is a compound which has sufficient structural similarity to a peptide so that the desirable properties of the peptide are retained by the mimetic. For example, peptide mimetics are already being used as protease inhibitors for treating HIV infection, as disclosed in Tung, et al., WO 94/05639, Vazquez, et al., WO 94/04491, Vazquez, et al., WO 94/10134 and Vaquez, et al., WO 94/04493. The entire relevant teachings of these publications are incorporated herein by reference. To be useful as a drug, a peptide mimetic should retain the biological activity of a peptide, but also have one or more properties which are improved compared with the peptide which is being mimicked. For example, some peptide mimetics are resistant to hydrolysis or to degradation in vivo. One strategy for preparing a peptide mimetic is to replace one or more amino acid residues in a peptide with a group which is structurally related to the amino acid residue(s) being replaced and which can form peptide bonds. The development of new amino acid derivatives which can be used to replace amino acid residues in peptides will advance the development of new peptide mimetic drugs.

Combinatorial libraries have great utility for identifying leads in drug discovery. The "Ugi" reaction, shown schematically below, is commonly used to generate combinatorial libraries.

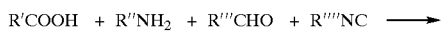

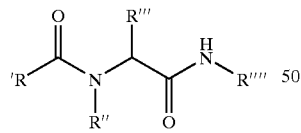

The ability to identify new, structurally diverse compounds which can participated in the Ugi reaction are needed to identify new drug leads from combinatorial libraries which are constructed using the this reaction.

SUMMARY OF THE INVENTION

The present invention includes novel isonitriles, diisonitriles, triamines, oxazolidines, oxazolines and imidazoles, and methods of preparing these novel compounds.

One embodiment of the present invention is a compound represented by Structural Formula I:

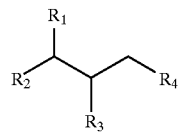

or salts thereof.

In Structural Formula I, $R_1$ is an aliphatic group, a substituted aliphatic group, an aromatic group or a substituted aromatic group. Preferably, $R_1$ is an amino acid side-chain or a protected amino acid side-chain.

$R_2$ is $-NR_5R_6$ or $-N^+{\equiv}C^-$.

Alternatively, $R_1$ and $R_2$, taken together with the methine group to which they are bonded, are a moiety represented by the following structural formula:

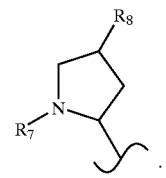

$R_3$ is $-NH_2$, $-OH$, $-OC(O)H$ or $-OR_9$.

$R_4$ is $-N^+{\equiv}C^-$, $-NH_2$, or $-NO_2$.

$R_5$, $R_6$ and $R_7$, are each, independently, $-H$ or an amine protecting group.

$R_8$ is $-H$, $-OH$ or $-OR_9$.

$R_9$ is an alcohol protecting group.

One embodiment of the present invention is an isonitrile represented by Structural Formula II:

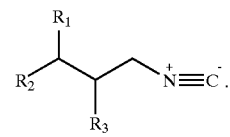

Isonitriles represented by Structural Formula II are prepared by dehydrating a N-alkyl formamide represented by Structural Formula III:

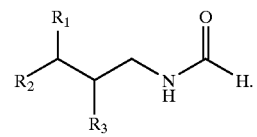

The N-alkyl formamide of Structural Formula III is prepared by formylating a starting material represented by Structural Formula IV:

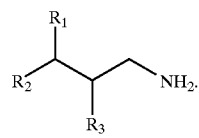

In Structural Formulas II, III and IV, $R_1$, $R_2$, and $R_3$ are defined as in Structural Formula I. In a preferred embodiment, $R_1$ is benzyl, sec-butyl, the side-chain of tryptophan, —$(CH_2)_4$—NH(t-butoxycarbonyl), —$CH_2$COO (t-butyl), —CH(O-benzyl)—$CH_3$, or —$(CH_2)_2$—S—$CH_3$; and $R_3$ is —OCH(O).

Another embodiment of the present invention is a 2-hydroxypropyl isonitrile represented by Structural Formula V:

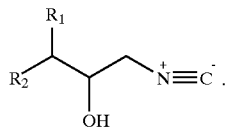
V.

Isonitriles represented by Structural Formula V are prepared by reacting a trialkylsilyl cyanide and $ZnI_2$ with a starting compound represented by Structural Formula VI:

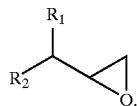
VI.

In Structural Formulas V and VI, $R_1$ and $R_2$ are as described form Structural Formula I.

Another embodiment of the present invention is a 2-amino-1-nitropropane represented by Structural Formula VII:

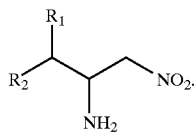
VII.

The 2-amino-1-nitropropanes represented by Structural Formula VII are prepared by reducing an oxime ether of a compound represented by Structural Formula VIII:

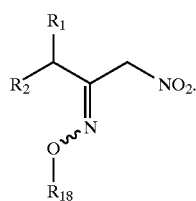
VIII.

In Structural Formulas VII and VIII, $R_1$ and $R_2$ are as described for Structural Formula I. $R_{18}$ is an aliphatic group, a substituted aliphatic group, an aromatic group or a substituted aromatic group. Preferably $R_{18}$ is a C1–C3 alkyl group.

Another embodiment of the present invention is an imidazole represented by Structural Formula IX:

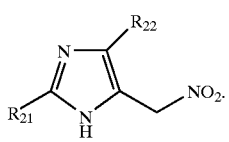
IX.

Imidazoles represented by Structural Formula IX are prepared by reacting an aliphatic carboxylic acid and an ammonium salt of the aliphatic carboxylic acid with a compound represented by Structural Formula X:

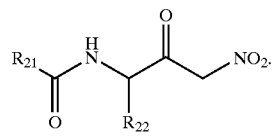
X.

In Structural Formulas IX and X, $R_{21}$, and $R_{22}$ are each, independently, —H, an aliphatic group, a substituted aliphatic group, an aromatic group or a substituted aromatic group. $R_{21}$ is preferably a C1–C4 straight chain or branched alkyl group. $R_{22}$ is preferably an aliphatic side-chain of a naturally occurring amino acid.

Another embodiment of the present invention is an oxazolidine represented by Structural Formula XI:

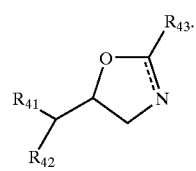
XI.

$R_{41}$ is an aliphatic group, a substituted aliphatic group, an aryl group or a substituted aryl group. $R_{41}$ is preferably the side-chain of a naturally occurring amino acid or a protected side-chain of a naturally occurring amino acid.

$R_{42}$ is —$NR_5R_6$.

Alternatively, $R_{41}$ and $R_{42}$, taken together with the methine group to which they are bonded, form a moiety represented by Structural Formula XII:

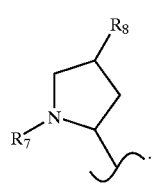
XII.

$R_{43}$ is an aliphatic group, a substituted aliphatic group, an aryl group or a substituted aryl group. $R_{43}$ is preferably a C1–C3 alkyl group or substituted alkyl group.

In Structural Formulas XI and XII, $R_5$, $R_6$, $R_7$ and $R_8$ are as described for Structural Formula I. In a preferred embodiment, one of $R_5$ and $R_6$ is —H.

The compounds represented by Structural Formula XI are prepared by reacting a 2-hydroxy-1-propylamine represented by Structural Formula XIII and a compound represented by Structural Formula XIV:

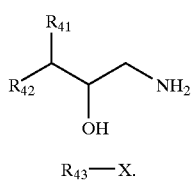

XIII.

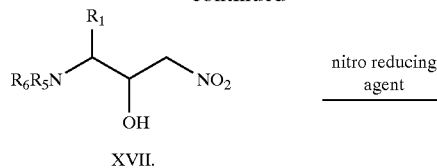

XVII.

XIV.

R<sub>43</sub>—X.

$R_{41-43}$ are as described for Structural Formula XI.

X is —CHO, —COOR or —C(=NH)OR. R is an aliphatic group, a substituted aliphatic group, an aryl group or a substituted aryl group. R is preferably a C1–C4 alkyl group.

The compounds of the present invention can be used as reagents in the Ugi reaction or to prepare peptide mimetics, and, consequently, can be used to identify new drug leads. The compounds of the present invention can be obtained in optically pure form from the disclosed methods, if the starting materials are optically pure. Using optically pure reagents in combinatorial reactions such as the Ugi reaction should result in conformationally restricted adducts which can be utilized to map the three-dimensional structure of receptor sites.

DETAILED DESCRIPTION OF THE INVENTION

The features and other details of the method of the invention will now be more particularly described and pointed out in the claims. It will be understood that the particular embodiments of the invention are shown by way of illustration and not as limitations of the invention. The principle features of this invention can be employed in various embodiments without departing from the scope of the invention. All parts and percentages are by weight unless otherwise specified.

Compounds represented by Structural Formulas I are derived from amino acid precursors. The amino alcohols can be prepared by a method summarized in Scheme I and described in detail in U.S. Pat. No. 5,475,138, the entire teachings of which are incorporated herein by reference. In Scheme I, $R_1$, $R_5$ and $R_6$ are as described above. The starting material in Scheme I, compound XV, is an amino acid wherein the amine functionality is protected. The compounds of the present invention represented by Structural Formula I are derived from compound XVIII of Scheme I.

Scheme I:
Synthesis of diaminoalcohols (Structural Formula XVIII) from an amino acid precursors.

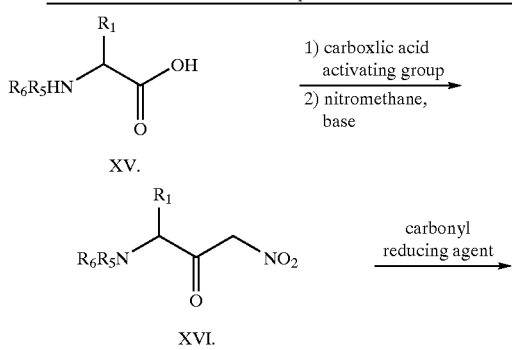

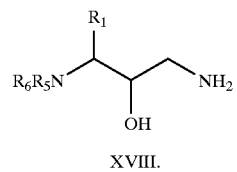

XVIII.

In a preferred embodiment of the present invention, $R_5$ and $R_6$ of Structural Formula XVIII are each —H and the alcohol group is protected. This compound is represented by Structural Formula XIX:

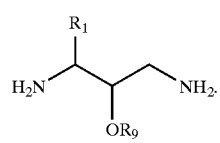

XIX.

Methods for protecting alcohols are known to those skilled in the art and can be found in Greene and Wuts, "Protective Groups in Organic Synthesis, $2^{nd}$," John Wiley & Sons (1991). A diamino compound represented by Structural Formula XIX can be formylated to form a compound represented by Structural Formula XX:

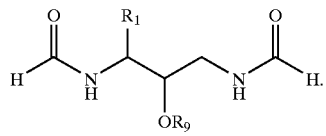

XX.

Compound XX can be dehydrated to form the diisonitrile represented by Structural Formula XXI:

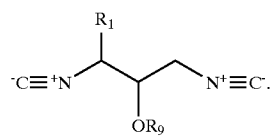

XXI.

In another preferred embodiment, the alcohol group of compound XVIII can be protected and the unprotected amine can be formylated to form a N-alkyl formamide represented by Structural Formula XXII:

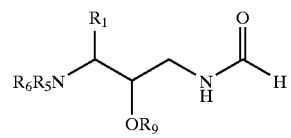

XXII.

The N-alkyl formamide represented by Structural Formula XXII can be dehydrated to form an isonitrile represented by Structural Formula XXIII:

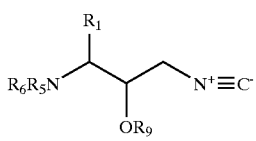

XXIII.

When the amino acid proline or a substituted proline is used as a starting material in Scheme I, the diaminoalcohol synthesized can be represented by Structural Formula XXIV:

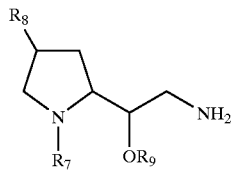

XXIV.

Compound XXIV can be formylated to form a compound represented by Structural Formula XXV:

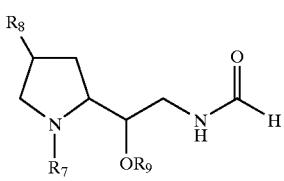

XXV.

A compound represented by Structural Formula XXV can be dehydrated to form an isonitrile represented by Structural Formula XXVI:

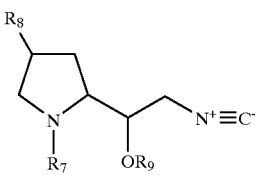

XXVI.

Procedures for carrying out the dehydration reaction to form an isonitrile, for example, compounds represented by Structural Formulas II, XXI, XXII or XXVI from an N-alkyl formamide, for example, compounds represented by Structural Formulas III, XX, XXII or XXV, respectively, are disclosed in "Organic Functional Group Preparations" S. R. Sandler and W. Karo, Volume III, $2^{nd}$ edition, Academic Press, Inc. San Diego, 1989, pages 206–235. The entire teachings of pages 206–235 in "Organic Functional Group Preparations" are incorporated herein by reference. Isonitriles are prepared by elimination of water from N-alkyl formamides. The elimination reaction is accomplished by treatment of the N-alkyl formamide with phosgene and a tertiary amine (see for review Hoffmann, et al., *Isonitrile Chemistry*, (1971), Academic Press, New York, p. 10–17; Ugi, et al., *Angew. Chem. Int. Ed. Engl.*, (1965), 4:472). Other reagents can also be used, for example, tosyl chloride in quinoline; phosporous oxychloride ($POCl_3$) and a tertiary amine; (chloromethylene) dimethylammonium chloride (($CH_3)_2N=CHCl^{30}$ $Cl^-$) (see Walborsky, et al., *J. Org. Chem.*, (1972), 37:187); diphosgene (ClC(O)C(O)Cl) (see Skorna and Ugi, *Angew. Chem. Int. Ed. Engl.* (1977); 16:259), 2-chloro-3-ethylbenzoxazolium tetrafluoroborate (see Echigo, et al., *Chem. Lett.*, (1977), 697); or a complex of triphenylphosphine-carbon tetrahalide-triethylamine (see Bestmann, et al., *Liebigs Ann. Chem.* (1968), 718:24).

As used herein "formylation" of an amine is addition of a formyl group (i.e., —C(O)H) to the amine. Procedures for formylating the amino compounds represented by Structural Formnulas IV, XVIII, XIX and XXIV to prepare N-alkyl formamides represented by Structural Formnulas III, XX, XXII and XXV, respectively, are described in Greene and Wuts, "Protective Groups in Organic Synthesis," John Wiley & Sons (1991), pages 349–350. For example, a primary or secondary amine can be formylated in about 78–90% yield by treating the amine with a solution of 98% formic acid and 2% acetic anhydride at 25° C. for 1 h (see Sheehan and Yang, *J. Am. Chem. Soc.*, (1958), 80:1154 and Jahngen, et al., *Synth. Commun.* (1982), 12:601). Primary or secondary amines can also be formylated in about 87–90% yield by treatment with formic acid and DCC in pyridine at 0° C. for 4 h (see Waki and Meienhofer, *J. Org. Chem.*, (1977), 42:2019). Another method of formylating a primary or secondary amine is by treatment with t-butyldimethylsilyl chloride, 4-dimethylaminopyridine and triethyl amine in dimethyl formamide at 35–60° C. This method yields the formylated amine in about 65–85% yield (Djuric, *J. Org. Chem.*, (1984), 49:1311). Other methods are described in Greene and Wuts, "Protective Groups in Organic Synthesis."

Isonitriles represented by Structural Formula V can also be prepared by reacting trimethylsilylcyanide (TMS-CN) and a catalytic amount of $ZnI_2$ with an epoxide represented by Structural Formula VI. The reaction is typically carried out in a polar aprotic solvent such as methylene chloride, chloroform or dichloroethane, preferably methylene chloride. The solvent is preferably dried before use. An excess of TMS-CN relative to the epoxide can be used, for example, from one to about ten equivalents of TMS-CN relative to epoxide, preferably from one to about two equivalents. The reaction is carried out at concentrations of from about 0.01 M to about 5.0 M, preferably 0.1 M to about 1.0 M, and at temperatures ranging from about 0° C. to about 80° C., preferably at the reflux temperature of methylene chloride.

Epoxides represented by Structural Formula VI can be prepared by methods disclosed in Vazquez, et al., WO 94/04491, the entire relevant teachings of which are incorporated herein by reference.

A 2-amino-3-nitropropane represented by Structural Formula VII can be prepared from, for example, an oxime ether represented by Structural Formula VIII using hydride reducing agents such as sodium borohydride, lithium borohydride, lithium aluminum hydride, lithium triethyl borohydride and the like, or by using a borane reducing agent such as diborane. The reaction is generally carried out in an ethereal solvent such as tetrahydrofuran, diethyl ether, glyme, diglyme or dioxane using from one to about twenty reducing equivalents, preferably from about one to about three reducing equivalents. Typically, reaction temperatures range from about –20° C. to about 50° C., and are preferably from about –5° C. to ambient temperature. The concentration of the reagents range from about 0.01 M to about 2.0 molar, preferably about 0.1 M to about 1.0 M. Specific conditions for carrying out this reaction are disclosed in WO 96/39399 by Sun, et al., the entire teachings of which are incorporated herein by reference.

The syn or anti geometric isomer of an oxime ether can be stereoselectively reduced to preferentially form one stereoisomer by performing the reduction in the presence of a suitable chiral auxiliary agent. "Chiral auxiliary agent" is a compound which, when added to a reaction mixture, results in a reaction having a higher degree of stereoselectivity than in the absence of the compound. For example, in the conversion of the oxime ether represented by Structural Formula VIII to the compound represented by Structural Formula VII, a larger enantiomeric excess of the 2S stereoisomer (or 2R stereoisomer) is formed in the presence of the chiral auxiliary agent than in its absence. Examples of suitable chiral auxiliary agents include chiral amines such as (−)-norephedrine, (+)-norephedrine, (−)-ephedrine, (+)-ephedrine and (+)-2-amino-1-(2-methylphenyl)-1-propanol and (−)-2-amino-1-(2-methylphenyl)-1-propanol. One geometric isomer of an oxime ether (e.g., syn) together with one enantiomer of a chiral auxiliary agent (e.g., (+)-ephedrine) will preferentially form one stereoisomer product (e.g., 2S). Using either the opposite oxime ether geometric isomer or the opposite chiral auxiliary enantiomer will preferentially form the opposite stereoisomer product (e.g., 2R). Using the opposite geometric isomer oxime ether and the opposite chiral auxiliary enantiomer will preferentially form the same stereoisomer product (e.g., 2S). Other suitable chiral auxiliary agents, as well as specific conditions for stereoselectively reducing an oxime ether, are disclosed in U.S. Pat. No. 5,200,561 to Konya, et al., Itsuno, et al., *J. Chem. Soc. Perkin Trans. I*, 1985:2039 and Sakito, et al., *Tetrahedron* 29:223 (1988), the entire teachings of which are incorporated herein by reference. Typically, between about 0.5 and about 1.0 moles of chiral auxiliary agent per mole of reducing agent are used.

Oxime ethers represented by Structural Formula VIII, which are used to form 2-amino-1-nitropropanes represented by Structural Formula VII can be prepared by reacting approximately equimolar amounts a nitroketone represented by Structural Formula XVI with the hydrochloride salt of $NH_2OR_{18}$ in pyridine.

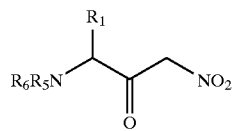

XVI.

$R_1$, $R_5$, and $R_6$ are as described for Structural Formula I, and $R_{18}$ is as described for Structural Formula VIII. Specific conditions for performing this reaction are described, for example, in Sun, et al., WO 96/39399. The syn and anti isomers can be separated by column chromatography. The prepartion of nitroketone starting materials are described in U.S. Pat. No. 5,475,138, the entire teachings of which are incorporated herein by reference.

The 2-amino-1-nitropropane represented by Structural Formula VII can be further reacted with a nitro group reducing agent to form a diamino compound represented by Structural Formula XXVII.

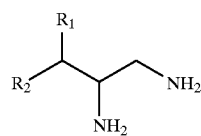

XXVII.

Reagents suitable for reducing a nitro group to an amine are well known in the art and include hydrogenation catalysts such as $PtO_2$ and Pd. The nitro compound is dissolved in an alcoholic or ethereal solvent under a hydrogen atmosphere (from about one to about 100 pounds per square inch) in the presence of the hydrogenation catalyst. Other nitro reducing agents include hydride reducing agents such as lithium aluminum hydride, lithium triethyl borohydride and lithium aluminum trimethoxy hydride. The procedure used to perform this reduction is similar to those described above for the reduction of the oxime ether, modified to include a suitable nitro reducing agents. Specific procedures are described in U.S. Pat. No. 5,475,138 and in Brown, et al., *Aldrichimica Acta*, 12:3 (1979) and references cited therein, the entire relevant teachings of which are incorporated herein by reference.

The compound represented by Structural Formula IX can be prepared by reacting an aliphatic carboxylic acid and an ammonium salt of the aliphatic carboxylic acid with a compound represented by Structural Formula X. Specific procedures for carrying out this reaction are provided in von Geldern, et al., *J. Med. Chem.*, 39:957 (1996), the entire teachings of which are hereby incorporated by reference.

The nitro group in the compounds represented by Structural Formula IX can be hydrogenated to form a product with an amine group. Suitable hydrogenation conditions are described hereinbelow. This amine product can be used as a reagent in the Ugi reaction to prepare new combinatorial libraries for drug discovery.

The compound represented by Structural Formula XI can be prepared by mixing an amino alcohol represented by Structural Formula XIII and a compound represented by Structural Formula XIV in a solvent such as acetonitrile, methylene chloride, chloroform or methanol (preferably an anhydrous solvent) and allowing the compounds to react. An excess of either reagent can be used. Preferably, a 5–10% excess of the compound represented by Structural Formula XIV is used. The reaction is typically performed at concentrations of between about 0.01 M to about 5.0 M of the , preferably from about 0.1 M to about 1.0 M at temperatures ranging from about 0° C. to about 70° C., preferably at about room temperature. Specific conditions for performing the reaction are provided in the Example.

Oxazolidines included in Structural Formula XI can be used as a reagent in the Ugi reaction to prepare new combinatorial libraries for drug discovery. For oxazolines included in Structural Formula XI, the amine represented by $R_{42}$ can be deprotected by standard means. The resulting compound has a free amine which can react in the Ugi reaction.

An "amino acid" is compound represented by $NH_2$—CHR—COOH, wherein R is —H, an aliphatic group, a substituted aliphatic group, an aromatic group or a substituted aromatic group. A "naturally-occurring amino acid" is found in nature. Examples include alanine, valine, leucine, isoleucine, aspartic acid, glutamic acid, serine, threonine, glutamine, asparagine, arginine, lysine, ornithine, proline, hydroxyproline, phenylalanine, tyrosine, tryptophan, cysteine, methionine and histidine. R is the side-chain of the amino acid. Examples of naturally occurring amino acid side-chains include methyl (alanine), isopropyl (valine), sec-butyl (isoleucine), —$CH_2CH$(—$CH_3$)$_2$ (leucine), benzyl (phenylalanine), p-hydroxybenzyl (tyrosine), —$CH_2OH$ (serine), —$CHOHCH_3$ (threonine), —$CH_2$-3-indoyl (tryptophan), —$CH_2COOH$ (aspartic acid), —$CH_2CH_2COOH$ (glutamic acid), —$CH_2C(O)NH_2$ (asparagine), —$CH_2CH_2C(O)NH_2$ (glutamine), —$CH_SSH$ (cysteine), —$CH_2CH_2SCH_3$ (methionine), —$(CH_2)_4NH_2$ (lysine), —$(CH_2)_3NH_2$ (ornithine), —$[(CH)_2]_4NHC(=NH)NH_2$ (arginine) and —$CH_2$-3-imidazoyl (histidine).

The side-chains of alanine, valine, leucine and isoleucine are aliphatic, i.e., contain only carbon and hydrogen, and are each referred to herein as "the aliphatic side-chain of a naturally occurring amino acid."

The side-chains of other naturally-occurring amino acids comprise a heteroatom-containing functional group, e.g., an alcohol (serine, tyrosine, hydroxyproline and threonine), an amine (lysine, ornithine, histidine and arginine), a thiol (cysteine) or a carboxylic acid (aspartic acid and glutamic acid). When the heteroatom-containing functional group is modified to include a protecting group, the side-chain is referred to as the "protected side-chain" of an amino acid.

The selection of a suitable protecting group depends upon the functional group being protected, the conditions to which the protecting group is being exposed and to other functional groups which may be present in the molecule. Suitable protecting groups for the functional groups discussed above are described in Greene and Wuts, "Protective Groups in Organic Synthesis", John Wiley & Sons (1991), the entire teachings of which are incorporated into this application by reference. The skilled artisan can select, using no more than routine experimentation, suitable protecting groups for use in the disclosed synthesis, including protecting groups other than those described below, as well as conditions for applying and removing the protecting groups.

Examples of suitable alcohol protecting groups include benzyl, allyl, trimethylsilyl, tert-butyldimethylsilyl, acetate, and the like. Benzyl is a preferred alcohol protecting group.

Examples of suitable amino protecting groups include benzyloxycarbonyl, tert-butoxycarbonyl, tert-butyl, benzyl and fluorenylmethyloxycarbonyl (Fmoc). Tert-butoxycarbonyl is a preferred amine protecting group.

Examples of suitable carboxylic acid protecting groups include tert-butyl, Fmoc, methyl, methoxylmethyl, trimethylsilyl, benzyloxymethyl, tert-butyldimethylsilyl and the like. Tert-butyl is a preferred carboxylic acid protecting group.

Examples of suitable thiol protecting groups include S-benzyl, S-tert-butyl, S-acetyl, S-methoxymethyl and the like.

Lysine, aspartate and threonine are examples of amino acid side-chains that are preferably protected. The following structures are examples of a protected lysine side-chain, a protected aspartate side-chain and a protected threonine side-chain, respectively:

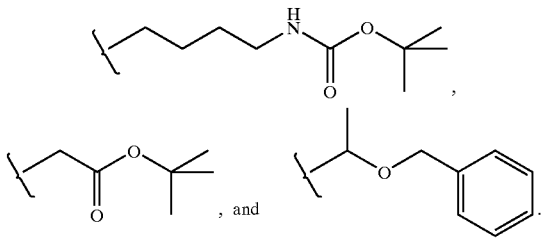

Aliphatic groups include straight chained, branched $C_1$–$C_8$, or cyclic $C_3$–$C_8$ hydrocarbons which are completely saturated or which contain one or more units of unsaturation. In one example, an aliphatic group is a C1–C4 alkyl group.

Aromatic groups include carbocyclic aromatic groups such as phenyl, 1-naphthyl, 2-naphthyl, 1-anthracyl and 2-anthracyl, and heterocyclic aromatic groups such as N-imidazolyl, 2-imidazole, 2-thienyl, 3-thienyl, 2-furanyl, 3-furanyl, 2-pyridyl, 3-pyridyl, 4-pyridyl, 2-pyrimidy, 4-pyrimidyl, 2-pyranyl, 3-pyranyl, 3-pyrazolyl, 4-pyrazolyl, 5-pyrazolyl, 2-pyrazinyl, 2-thiazole, 4-thiazole, 5-thiazole, 2-oxazolyl, 4-oxazolyl and 5-oxazolyl.

Aromatic groups also include fused polycyclic aromatic ring systems in which a carbocyclic aromatic ring or heteroaryl ring is fused to one or more other heteroaryl rings. Examples include 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl, 3-isoindolyl, and acridintyl.

Preferred aromatic groups include the following groups:

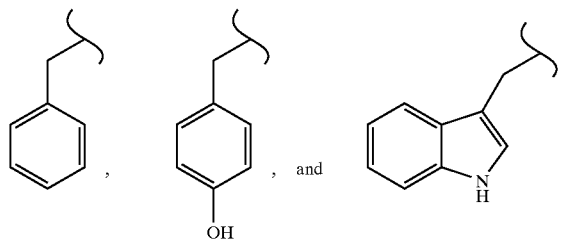

Suitable substituents for an aryl group and aliphatic group are those which are compatible with the disclosed reactions, i.e., do not significantly reduce the yield of the reactions and do not cause a significant amount of side reactions. Suitable substituents generally include aliphatic groups, substituted aliphatic groups, aryl groups, halogens, halogenated alkyl groups (e.g., trihalomethyl), nitro, nitrile, —CONHR, —CON(R)$_2$, —OR, —SR, —S(O)R, —S(O)$_2$R, wherein each R is independently an aliphatic group, or an aryl group. Although certain functional groups may not be compatible with one or more of the disclosed reactions, these functional groups may be present in a protected form. The protecting group can then be removed to regenerate the original functional group. The skilled artisan will be able to select, using no more than routine experimentation, protecting groups which are compatible with the disclosed reactions.

Also included in the present invention are physiologically acceptable salts of the compounds represented by Structural Formulas I, II, V, VII, IX and XI. Salts of compounds containing an amine or other basic group can be obtained, for example, by reacting with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium, potassium and the like.

In the structural formulas depicted herein, the single or double bond by which a chemical group or moiety is connected to the remainder of the molecule or compound is indicated by the following symbol:

For example, the corresponding symbol in Structural Formula XII indicates that the nitrogen-bonded methine carbon in the pyrollidine ring, is connected to the oxizolidine ring in Structural Formula XI by a single covalent bond.

An Ugi Reaction can be performed by mixing an amine, a carboxylic acid, an isonitrile and an aldehyde or ketone in a suitable solvent such as acetonitrile, methanol or dimethylsulfoxide at a concentration of about 250 mM for each reagent. Approximately equimolar amounts of each reagent are generally used. The reaction is typically carried out at temperatures between about 20° C. and about 60° C., and preferably at room temperature.

The invention is illustrated by the following example which are not intended to be limiting in any way.

Exemplification

EXAMPLE

Preparation of an Oxazolidine Represented by Structural Formula XXVIII

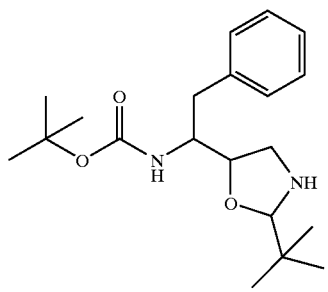

XXVIII.

| Chemical name, purity | Amount | mmoles |
|---|---|---|
| 1-Amino-3-(S)-tert-butylcarbamido-2-(R)-hydroxy-4-phenylbutane | 140.0 mg | 0.5 |
| Trimethylacetaldehyde, 97% | 60 µl | 0.55 |
| Acetonitrile, anhydrous, 99% | 30 ml | — |

Procedure

Trimethylacetaldehyde was added to a suspension of 1-amino-3-(S)-tert-butylcarbamido-2-(R)-hydroxy-4-phenylbutane in anhydrous acetonitrile (2 mL). The mixture became thinner as some of the solid went into solution, but after awhile became thick as a new solid-started to form. More acetonitrile (1 mL) was added to facilitate stirring. After 5 h, a sample was withdrawn and dried under high vacuum. $^1$H NMR analysis indicated that oxazolidine formation had proceeded to an appreciable extent. The reaction was allowed to stir at room temperature overnight.

The white precipitate was collected by suction filtration, washed with a small amount of anhydrous acetonitrile (~1 mL) and dried under high vacuum. The filtrate was concentrated to dryness to give a white solid which was dried under high vacuum. The combined yield was 164.3 mg (94.4%). This solid could be used without any further manipulation.

Equivalents

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of preparing an imidazole represented by the following structural formula:

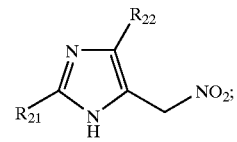

or salts thereof, wherein:

$R_{21}$ and $R_{22}$ are each, independently, —H, an aliphatic group, a substituted aliphatic group, an aromatic group or a substituted aromatic group, comprising the step of reacting an aliphatic carboxylic acid and an ammonium salt of the aliphatic carboxylic acid with a compound represented by the following structural formula:

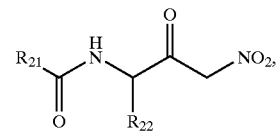

thereby forming said imidazole.

2. The method of claim 1, wherein:

$R_{21}$ is a C1–C4 alkyl; and $R_{22}$ is an aliphatic side-chain of a naturally occurring amino acid.

3. A compound represented by the following structural formula:

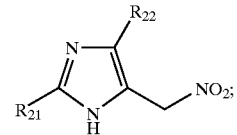

or salts thereof, wherein:

$R_{21}$ and $R_{22}$ are each, independently, —H, an aliphatic group, a substituted aliphatic group, an aromatic group or a substituted aromatic group.

* * * * *